US008783250B2

(12) United States Patent
Jafari et al.

(10) Patent No.: US 8,783,250 B2
(45) Date of Patent: Jul. 22, 2014

(54) METHODS AND SYSTEMS FOR TRANSITORY VENTILATION SUPPORT (75) Inventors: Mehdi M. Jafari, Laguna Hills, CA (US); Peter R. Doyle, Vista, CA (US); Rhomere S. Jimenez, San Diego, CA (US); Jeffrey K. Aviano, Escondido, CA (US)

(73) Assignee: Covidien LP, Mansfield, MA (US)

( * ) Notice: Subject to any disclaimer, the term of this patent is extended or adjusted under 35 U.S.C. 154(b) by 528 days.

(21) Appl. No.: 13/035,977

(22) Filed: Feb. 27, 2011

(65) Prior Publication Data
US 2012/0216810 A1      Aug. 30, 2012

(51) Int. Cl.
*A61M 16/00*      (2006.01)
*A61B 7/00*       (2006.01)

(52) U.S. Cl.
USPC .................................................. 128/204.23

(58) Field of Classification Search
USPC ............. 128/204.23, 204.18, 204.22, 202.22, 128/204.21, 204.26, 205.11, 205.24
See application file for complete search history.

(56) References Cited

U.S. PATENT DOCUMENTS

| | | |
|---|---|---|
| 4,444,201 A | 4/1984 | Itoh |
| 4,752,089 A | 6/1988 | Carter |
| 4,921,642 A | 5/1990 | LaTorraca |
| 4,954,799 A | 9/1990 | Kumar |
| 5,016,626 A | 5/1991 | Jones |
| 5,044,362 A | 9/1991 | Younes |
| 5,057,822 A | 10/1991 | Hoffman |
| 5,072,737 A | 12/1991 | Goulding |
| 5,080,093 A | 1/1992 | Raabe et al. |
| 5,107,830 A | 4/1992 | Younes |
| 5,129,390 A | 7/1992 | Chopin et al. |
| 5,148,802 A | 9/1992 | Sanders et al. |
| 5,150,291 A | 9/1992 | Cummings et al. |
| 5,161,525 A | 11/1992 | Kimm et al. |
| 5,165,398 A | 11/1992 | Bird |
| 5,211,170 A | 5/1993 | Press |
| 5,235,973 A | 8/1993 | Levinson |
| 5,237,987 A | 8/1993 | Anderson et al. |
| 5,239,995 A | 8/1993 | Estes et al. |
| 5,271,389 A | 12/1993 | Isaza et al. |
| 5,279,549 A | 1/1994 | Ranford |
| 5,299,568 A | 4/1994 | Forare et al. |

(Continued)

FOREIGN PATENT DOCUMENTS

| | | |
|---|---|---|
| EP | 521515 A1 | 1/1993 |
| EP | 996358 A4 | 5/2000 |

(Continued)

OTHER PUBLICATIONS

Am J Respir Crit Care Med 2001;163:829-39. http://ajrccm.atsjournals.org/cgi/reprint/164/1/50, May 17, 2000, Title: A Method for Noninvasive Determination of Inspiratory Resistance during Proportional Assist Ventilation.

Am J Respir Crit Care Med 2001;164:50-60 http://ajrccm.atsjournals.org/cgi/reprint/164/1/50, Oct. 12, 2000, Title: A Method for Measuring Passive Elastance during Proportional Assist Ventilation.

(Continued)

*Primary Examiner* — Kristen Matter
*Assistant Examiner* — Mark Wardas (57) ABSTRACT

This disclosure describes systems and methods for providing a transitory ventilation support breath type during ventilation of a patient. The disclosure describes a novel breath type that provides for a beneficial transition between an assist breath type and an effort-based breath type and/or a breath type that is beneficial for weak patients.

6 Claims, 3 Drawing Sheets

(56) References Cited

U.S. PATENT DOCUMENTS

| | | |
|---|---|---|
| 5,301,921 A | 4/1994 | Kumar |
| 5,303,698 A | 4/1994 | Tobia et al. |
| 5,303,700 A | 4/1994 | Weismann et al. |
| 5,306,808 A | 4/1994 | Wakimasu et al. |
| 5,307,794 A | 5/1994 | Rauterkus et al. |
| 5,307,795 A | 5/1994 | Whitwam et al. |
| 5,316,009 A | 5/1994 | Yamada |
| 5,319,540 A | 6/1994 | Isaza et al. |
| 5,320,093 A | 6/1994 | Raemer |
| 5,322,057 A | 6/1994 | Raabe et al. |
| 5,323,772 A | 6/1994 | Linden et al. |
| 5,325,861 A | 7/1994 | Goulding |
| 5,333,606 A | 8/1994 | Schneider et al. |
| 5,335,650 A | 8/1994 | Shaffer et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,373,842 A | 12/1994 | Olsson et al. |
| 5,383,449 A | 1/1995 | Forare et al. |
| 5,385,142 A | 1/1995 | Brady et al. |
| 5,390,666 A | 2/1995 | Kimm et al. |
| 5,395,301 A | 3/1995 | Russek |
| 5,398,676 A | 3/1995 | Press et al. |
| 5,398,682 A | 3/1995 | Lynn |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,429,123 A | 7/1995 | Shaffer et al. |
| 5,433,193 A | 7/1995 | Sanders et al. |
| 5,438,980 A | 8/1995 | Phillips |
| 5,443,075 A | 8/1995 | Holscher |
| 5,471,977 A | 12/1995 | Olsson et al. |
| 5,492,113 A | 2/1996 | Estes et al. |
| 5,507,282 A | 4/1996 | Younes |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| RE35,295 E | 7/1996 | Estes et al. |
| 5,531,221 A | 7/1996 | Power |
| 5,535,738 A | 7/1996 | Estes et al. |
| 5,537,999 A | 7/1996 | Dearman et al. |
| 5,540,220 A | 7/1996 | Gropper et al. |
| 5,540,222 A | 7/1996 | Younes |
| 5,542,415 A | 8/1996 | Brody |
| 5,542,416 A | 8/1996 | Chalvignac |
| 5,544,674 A | 8/1996 | Kelly |
| 5,549,106 A | 8/1996 | Gruenke et al. |
| 5,551,418 A | 9/1996 | Estes et al. |
| 5,558,086 A | 9/1996 | Smith et al. |
| 5,564,416 A | 10/1996 | Jones |
| 5,582,163 A | 12/1996 | Bonassa |
| 5,596,984 A | 1/1997 | O'Mahoney et al. |
| 5,598,838 A | 2/1997 | Servidio et al. |
| 5,603,316 A | 2/1997 | Coufal et al. |
| 5,606,968 A | 3/1997 | Mang |
| 5,630,411 A | 5/1997 | Holscher |
| 5,632,269 A | 5/1997 | Zdrojkowski |
| 5,632,270 A | 5/1997 | O'Mahoney et al. |
| 5,642,726 A | 7/1997 | Owens et al. |
| 5,645,048 A | 7/1997 | Brodsky et al. |
| 5,647,351 A | 7/1997 | Weismann et al. |
| 5,651,361 A | 7/1997 | Dearman et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,692,497 A | 12/1997 | Schnitzer et al. |
| 5,715,812 A | 2/1998 | Deighan et al. |
| 5,720,278 A | 2/1998 | Lachmann et al. |
| 5,735,267 A | 4/1998 | Tobia |
| 5,740,797 A | 4/1998 | Dickson |
| 5,762,480 A | 6/1998 | Adahan |
| 5,765,558 A | 6/1998 | Psaros et al. |
| 5,771,884 A | 6/1998 | Yarnall et al. |
| 5,791,339 A | 8/1998 | Winter |
| 5,794,615 A | 8/1998 | Estes |
| 5,794,986 A | 8/1998 | Gansel et al. |
| 5,803,065 A | 9/1998 | Zdrojkowski et al. |
| 5,807,245 A | 9/1998 | Aldestam et al. |
| 5,813,399 A | 9/1998 | Isaza et al. |
| 5,814,086 A | 9/1998 | Hirschberg et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,868,133 A | 2/1999 | DeVries et al. |
| 5,876,352 A | 3/1999 | Weismann |
| 5,878,744 A | 3/1999 | Pfeiffer |
| 5,881,717 A | 3/1999 | Isaza |
| 5,881,723 A | 3/1999 | Wallace et al. |
| 5,884,622 A | 3/1999 | Younes |
| 5,884,623 A | 3/1999 | Winter |
| 5,909,731 A | 6/1999 | O'Mahony et al. |
| 5,911,218 A | 6/1999 | DiMarco |
| 5,915,379 A | 6/1999 | Wallace et al. |
| 5,915,380 A | 6/1999 | Wallace et al. |
| 5,915,381 A | 6/1999 | Nord |
| 5,915,382 A | 6/1999 | Power |
| 5,918,597 A | 7/1999 | Jones et al. |
| 5,921,238 A | 7/1999 | Bourdon |
| 5,927,274 A | 7/1999 | Servidio et al. |
| 5,931,160 A | 8/1999 | Gilmore et al. |
| 5,934,274 A | 8/1999 | Merrick et al. |
| 5,937,853 A | 8/1999 | Ström |
| 5,944,680 A | 8/1999 | Christopherson et al. |
| 5,970,975 A | 10/1999 | Estes et al. |
| 6,015,388 A | 1/2000 | Sackner et al. |
| 6,019,100 A | 2/2000 | Alving et al. |
| 6,024,089 A | 2/2000 | Wallace et al. |
| 6,029,664 A | 2/2000 | Zdrojkowski et al. |
| 6,041,780 A | 3/2000 | Richard et al. |
| 6,047,860 A | 4/2000 | Sanders |
| 6,068,602 A | 5/2000 | Tham et al. |
| 6,076,523 A | 6/2000 | Jones et al. |
| 6,095,140 A | 8/2000 | Poon et al. |
| 6,105,575 A | 8/2000 | Estes et al. |
| 6,109,260 A | 8/2000 | Bathe |
| 6,116,240 A | 9/2000 | Merrick et al. |
| 6,116,464 A | 9/2000 | Sanders |
| 6,123,073 A | 9/2000 | Schlawin et al. |
| 6,131,571 A | 10/2000 | Lampotang et al. |
| 6,131,572 A | 10/2000 | Heinonen |
| 6,135,105 A | 10/2000 | Lampotang et al. |
| 6,135,106 A | 10/2000 | Dirks et al. |
| 6,142,150 A | 11/2000 | O'Mahony |
| 6,152,129 A | 11/2000 | Berthon-Jones |
| 6,152,133 A | 11/2000 | Psaros et al. |
| 6,158,432 A | 12/2000 | Biondi et al. |
| 6,158,433 A | 12/2000 | Ong et al. |
| 6,161,539 A | 12/2000 | Winter |
| 6,192,885 B1 | 2/2001 | Jalde |
| 6,196,222 B1 | 3/2001 | Heinonen et al. |
| 6,213,119 B1 | 4/2001 | Brydon et al. |
| 6,220,245 B1 | 4/2001 | Takabayashi et al. |
| 6,230,708 B1 | 5/2001 | Radko |
| 6,240,919 B1 | 6/2001 | MacDonald |
| 6,257,234 B1 | 7/2001 | Sun |
| 6,269,812 B1 | 8/2001 | Wallace et al. |
| 6,273,444 B1 | 8/2001 | Power |
| 6,279,569 B1 | 8/2001 | Berthon-Jones |
| 6,283,119 B1 | 9/2001 | Bourdon |
| 6,305,372 B1 | 10/2001 | Servidio |
| 6,305,373 B1 | 10/2001 | Wallace et al. |
| 6,305,374 B1 | 10/2001 | Zdrojkowski et al. |
| 6,308,703 B1 | 10/2001 | Alving et al. |
| 6,308,706 B1 | 10/2001 | Lammers et al. |
| 6,321,748 B1 | 11/2001 | O'Mahony |
| 6,325,785 B1 | 12/2001 | Babkes et al. |

(56) References Cited

U.S. PATENT DOCUMENTS

| | | |
|---|---|---|
| 6,345,619 B1 | 2/2002 | Finn |
| 6,357,438 B1 | 3/2002 | Hansen |
| 6,360,745 B1 | 3/2002 | Wallace et al. |
| 6,360,790 B1 | 3/2002 | Ward et al. |
| 6,369,838 B1 | 4/2002 | Wallace et al. |
| 6,390,091 B1 | 5/2002 | Banner et al. |
| 6,390,988 B1 | 5/2002 | Robinson |
| 6,412,483 B1 | 7/2002 | Jones et al. |
| 6,427,689 B1 | 8/2002 | Estes et al. |
| 6,439,229 B1 | 8/2002 | Du et al. |
| 6,450,968 B1 | 9/2002 | Wallen et al. |
| 6,461,315 B1 | 10/2002 | Gattinoni |
| 6,467,477 B1 | 10/2002 | Frank et al. |
| 6,467,478 B1 | 10/2002 | Merrick et al. |
| 6,467,479 B1 | 10/2002 | Albert et al. |
| 6,484,719 B1 | 11/2002 | Berthon-Jones |
| 6,523,538 B1 | 2/2003 | Wikefeldt |
| 6,526,970 B2 | 3/2003 | DeVries et al. |
| 6,532,956 B2 | 3/2003 | Hill |
| 6,532,957 B2 | 3/2003 | Berthon-Jones |
| 6,539,940 B2 | 4/2003 | Zdrojkowski |
| 6,546,930 B1 | 4/2003 | Emerson et al. |
| 6,547,743 B2 | 4/2003 | Brydon |
| 6,553,991 B1 | 4/2003 | Isaza |
| 6,553,992 B1 | 4/2003 | Berthon-Jones et al. |
| 6,557,553 B1 | 5/2003 | Borrello |
| 6,564,798 B1 | 5/2003 | Jalde |
| 6,571,795 B2 | 6/2003 | Bourdon |
| 6,571,796 B2 | 6/2003 | Banner et al. |
| 6,575,163 B1 | 6/2003 | Berthon-Jones |
| 6,575,164 B1 | 6/2003 | Jaffe et al. |
| 6,578,575 B1 | 6/2003 | Jonson |
| 6,588,422 B1 | 7/2003 | Berthon-Jones et al. |
| 6,588,423 B1 | 7/2003 | Sinderby |
| 6,601,583 B2 | 8/2003 | Pessala et al. |
| 6,609,517 B1 | 8/2003 | Estes et al. |
| 6,622,726 B1 | 9/2003 | Du |
| 6,626,175 B2 | 9/2003 | Jafari et al. |
| 6,629,527 B1 | 10/2003 | Estes et al. |
| 6,631,716 B1 | 10/2003 | Robinson et al. |
| 6,644,310 B1 | 11/2003 | Delache et al. |
| 6,651,652 B1 | 11/2003 | Ward |
| 6,651,657 B1 | 11/2003 | Manigel et al. |
| 6,659,101 B2 | 12/2003 | Berthon-Jones |
| 6,659,961 B2 | 12/2003 | Robinson |
| 6,668,824 B1 | 12/2003 | Isaza et al. |
| 6,672,300 B1 | 1/2004 | Grant |
| 6,675,801 B2 | 1/2004 | Wallace et al. |
| 6,679,258 B1 | 1/2004 | Ström |
| 6,681,643 B2 | 1/2004 | Heinonen |
| 6,688,307 B2 | 2/2004 | Berthon-Jones |
| 6,689,091 B2 | 2/2004 | Bui et al. |
| 6,694,978 B1 | 2/2004 | Bennarsten |
| 6,718,974 B1 | 4/2004 | Moberg |
| 6,725,447 B1 | 4/2004 | Gilman et al. |
| 6,739,337 B2 | 5/2004 | Isaza |
| 6,745,771 B2 | 6/2004 | Castor et al. |
| 6,752,766 B2 | 6/2004 | Kowallik et al. |
| 6,752,772 B2 | 6/2004 | Kahn |
| 6,755,193 B2 | 6/2004 | Berthon-Jones et al. |
| 6,758,217 B1 | 7/2004 | Younes |
| 6,761,167 B1 | 7/2004 | Nadjafizadeh et al. |
| 6,761,168 B1 | 7/2004 | Nadjafizadeh et al. |
| 6,763,829 B2 | 7/2004 | Jaffe et al. |
| 6,796,305 B1 | 9/2004 | Banner et al. |
| 6,805,118 B2 | 10/2004 | Brooker et al. |
| 6,810,876 B2 | 11/2004 | Berthon-Jones |
| 6,814,074 B1 | 11/2004 | Nadjafizadeh et al. |
| 6,820,613 B2 | 11/2004 | Wenkebach et al. |
| 6,820,618 B2 | 11/2004 | Banner et al. |
| 6,823,866 B2 | 11/2004 | Jafari et al. |
| 6,834,647 B2 | 12/2004 | Blair et al. |
| 6,837,241 B2 | 1/2005 | Samzelius |
| 6,837,242 B2 | 1/2005 | Younes |
| 6,840,240 B1 | 1/2005 | Berthon-Jones et al. |
| 6,854,462 B2 | 2/2005 | Berthon-Jones et al. |
| 6,860,264 B2 | 3/2005 | Christopher |
| 6,860,265 B1 | 3/2005 | Emerson |
| 6,860,858 B2 | 3/2005 | Green et al. |
| 6,866,040 B1 | 3/2005 | Bourdon |
| 6,877,511 B2 | 4/2005 | DeVries et al. |
| 6,910,480 B1 | 6/2005 | Berthon-Jones |
| 6,915,803 B2 | 7/2005 | Berthon-Jones et al. |
| 6,920,875 B1 | 7/2005 | Hill et al. |
| 6,920,878 B2 | 7/2005 | Sinderby et al. |
| 6,932,084 B2 | 8/2005 | Estes et al. |
| 6,948,497 B2 | 9/2005 | Zdrojkowski et al. |
| 6,960,854 B2 | 11/2005 | Nadjafizadeh et al. |
| 6,976,487 B1 | 12/2005 | Melker et al. |
| 6,990,980 B2 | 1/2006 | Richey, II |
| 6,997,881 B2 | 2/2006 | Green et al. |
| 7,000,612 B2 | 2/2006 | Jafari et al. |
| 7,001,339 B2 | 2/2006 | Lin |
| 7,001,340 B2 | 2/2006 | Lin |
| 7,011,091 B2 | 3/2006 | Hill et al. |
| 7,013,892 B2 | 3/2006 | Estes et al. |
| 7,021,310 B1 | 4/2006 | Sinderby et al. |
| 7,036,504 B2 | 5/2006 | Wallace et al. |
| 7,040,321 B2 | 5/2006 | Gobel |
| 7,055,522 B2 | 6/2006 | Berthon-Jones |
| 7,066,173 B2 | 6/2006 | Banner et al. |
| 7,066,176 B2 | 6/2006 | Jaffe et al. |
| 7,077,131 B2 | 7/2006 | Hansen |
| RE39,225 E | 8/2006 | Isaza et al. |
| 7,100,607 B2 | 9/2006 | Zdrojkowski |
| 7,100,609 B2 | 9/2006 | Berthon-Jones et al. |
| 7,117,438 B2 | 10/2006 | Wallace et al. |
| 7,128,069 B2 | 10/2006 | Farrugia et al. |
| 7,137,389 B2 | 11/2006 | Berthon-Jones |
| 7,152,598 B2 | 12/2006 | Morris et al. |
| 7,156,095 B2 | 1/2007 | Melker et al. |
| 7,162,296 B2 | 1/2007 | Leonhardt et al. |
| 7,191,780 B2 | 3/2007 | Faram |
| 7,210,478 B2 | 5/2007 | Banner et al. |
| 7,226,427 B2 | 6/2007 | Steen |
| 7,246,618 B2 | 7/2007 | Habashi |
| 7,255,103 B2 | 8/2007 | Bassin |
| 7,270,126 B2 | 9/2007 | Wallace et al. |
| 7,270,128 B2 | 9/2007 | Berthon-Jones et al. |
| 7,275,540 B2 | 10/2007 | Bolam |
| 7,296,573 B2 | 11/2007 | Estes et al. |
| 7,347,205 B2 | 3/2008 | Levi |
| 7,367,337 B2 | 5/2008 | Berthon-Jones et al. |
| 7,369,757 B2 | 5/2008 | Farbarik |
| 7,370,650 B2 | 5/2008 | Nadjafizadeh et al. |
| 7,422,015 B2 | 9/2008 | Delisle et al. |
| 7,425,201 B2 | 9/2008 | Euliano et al. |
| 7,428,902 B2 | 9/2008 | Du et al. |
| 7,460,959 B2 | 12/2008 | Jafari |
| 7,484,508 B2 | 2/2009 | Younes |
| 7,487,773 B2 | 2/2009 | Li |
| 7,487,774 B2 | 2/2009 | Acker |
| 7,509,957 B2 | 3/2009 | Duquette et al. |
| 7,520,279 B2 | 4/2009 | Berthon-Jones |
| 7,523,752 B2 | 4/2009 | Montgomery et al. |
| 7,549,421 B2 | 6/2009 | Levi et al. |
| 7,556,038 B2 | 7/2009 | Kirby et al. |
| 7,559,326 B2 | 7/2009 | Smith et al. |
| 7,572,225 B2 | 8/2009 | Stahmann et al. |
| 7,574,246 B2 | 8/2009 | Krebs et al. |
| 7,584,752 B2 | 9/2009 | Garber et al. |
| 7,588,033 B2 | 9/2009 | Wondka |
| 7,588,543 B2 | 9/2009 | Euliano et al. |
| 7,594,508 B2 | 9/2009 | Doyle |
| 7,617,824 B2 | 11/2009 | Doyle |
| 7,621,270 B2 | 11/2009 | Morris et al. |
| 7,644,713 B2 | 1/2010 | Berthon-Jones |
| 7,654,802 B2 | 2/2010 | Crawford, Jr. et al. |
| 7,669,594 B2 | 3/2010 | Downie |
| 7,669,598 B2 | 3/2010 | Rick et al. |
| 7,678,061 B2 | 3/2010 | Lee et al. |
| 7,694,677 B2 | 4/2010 | Tang |
| 7,717,110 B2 | 5/2010 | Kane et al. |
| 7,717,113 B2 | 5/2010 | Andrieux |

(56) References Cited

U.S. PATENT DOCUMENTS

| | | | |
|---|---|---|---|
| 7,721,736 B2 | 5/2010 | Urias et al. |
| 7,722,546 B2 | 5/2010 | Madaus et al. |
| D618,356 S | 6/2010 | Ross |
| 7,727,160 B2 | 6/2010 | Green et al. |
| 7,731,663 B2 | 6/2010 | Averina et al. |
| 7,770,578 B2 | 8/2010 | Estes et al. |
| 7,775,207 B2 | 8/2010 | Jaffe et al. |
| 7,784,461 B2 | 8/2010 | Figueiredo et al. |
| 7,798,145 B2 | 9/2010 | Weismann |
| 7,809,442 B2 | 10/2010 | Bolea et al. |
| 7,810,496 B2 | 10/2010 | Estes et al. |
| 7,814,906 B2 | 10/2010 | Moretti |
| 7,819,815 B2 | 10/2010 | Younes |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2002/0023640 A1 | 2/2002 | Nightengale |
| 2002/0026941 A1 | 3/2002 | Biondi et al. |
| 2002/0185126 A1 | 12/2002 | Krebs |
| 2002/0195105 A1 | 12/2002 | Blue et al. |
| 2003/0125662 A1 | 7/2003 | Bui |
| 2003/0145853 A1 | 8/2003 | Muellner |
| 2003/0172929 A1 | 9/2003 | Muellner |
| 2004/0016431 A1 | 1/2004 | Preveyraud |
| 2004/0159323 A1 | 8/2004 | Schmidt et al. |
| 2004/0187864 A1 | 9/2004 | Adams |
| 2004/0200477 A1 | 10/2004 | Bleys et al. |
| 2005/0022809 A1 | 2/2005 | Wondka |
| 2005/0027252 A1 | 2/2005 | Boukas |
| 2005/0039748 A1 | 2/2005 | Andrieux |
| 2005/0098179 A1 | 5/2005 | Burton et al. |
| 2005/0109339 A1 | 5/2005 | Stahmann et al. |
| 2005/0139212 A1 | 6/2005 | Bourdon |
| 2005/0217671 A1 | 10/2005 | Fisher et al. |
| 2005/0241639 A1 | 11/2005 | Zilberg |
| 2005/0279358 A1 | 12/2005 | Richey, II |
| 2005/0284469 A1 | 12/2005 | Tobia et al. |
| 2006/0011195 A1 | 1/2006 | Zarychta |
| 2006/0094972 A1 | 5/2006 | Drew |
| 2006/0102180 A1 | 5/2006 | Berthon-Jones |
| 2006/0174884 A1 | 8/2006 | Habashi |
| 2006/0249148 A1 | 11/2006 | Younes |
| 2006/0249155 A1 | 11/2006 | Gambone |
| 2006/0272642 A1 | 12/2006 | Chalvignac |
| 2006/0276718 A1 | 12/2006 | Madaus et al. |
| 2006/0278221 A1 | 12/2006 | Schermeier et al. |
| 2006/0278223 A1 | 12/2006 | Younes |
| 2006/0283450 A1 | 12/2006 | Shissler et al. |
| 2006/0283451 A1 | 12/2006 | Albertelli |
| 2007/0000494 A1 | 1/2007 | Banner et al. |
| 2007/0017515 A1 | 1/2007 | Wallace et al. |
| 2007/0017518 A1 | 1/2007 | Farrugia et al. |
| 2007/0028921 A1 | 2/2007 | Banner et al. |
| 2007/0044796 A1 | 3/2007 | Zdrojkowski et al. |
| 2007/0077200 A1 | 4/2007 | Baker |
| 2007/0151563 A1 | 7/2007 | Ozaki et al. |
| 2007/0163590 A1 | 7/2007 | Bassin |
| 2007/0181122 A1 | 8/2007 | Mulier |
| 2007/0186928 A1 | 8/2007 | Be'Eri |
| 2007/0191787 A1 | 8/2007 | Lim et al. |
| 2007/0208267 A1 | 9/2007 | Schmid et al. |
| 2007/0221222 A1 | 9/2007 | Lurie |
| 2007/0221224 A1 | 9/2007 | Pittman et al. |
| 2007/0225623 A1 | 9/2007 | Freeman |
| 2007/0227537 A1 | 10/2007 | Bemister et al. |
| 2007/0227538 A1 | 10/2007 | Scholler et al. |
| 2007/0272241 A1 | 11/2007 | Sanborn et al. |
| 2007/0277825 A1 | 12/2007 | Bordewick et al. |
| 2007/0284361 A1 | 12/2007 | Nadjafizadeh et al. |
| 2008/0000475 A1 | 1/2008 | Hill |
| 2008/0000478 A1 | 1/2008 | Matthiessen et al. |
| 2008/0011294 A1 | 1/2008 | Heesch et al. |
| 2008/0029096 A1 | 2/2008 | Kollmeyer et al. |
| 2008/0033304 A1 | 2/2008 | Dalal et al. |
| 2008/0035146 A1 | 2/2008 | Crabb |
| 2008/0041382 A1 | 2/2008 | Matthews et al. |
| 2008/0053441 A1* | 3/2008 | Gottlib et al. ............ 128/204.23 |
| 2008/0053443 A1 | 3/2008 | Estes et al. |
| 2008/0053444 A1 | 3/2008 | Estes et al. |
| 2008/0072896 A1 | 3/2008 | Setzer et al. |
| 2008/0072901 A1 | 3/2008 | Habashi |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0115786 A1 | 5/2008 | Sinderby et al. |
| 2008/0125828 A1 | 5/2008 | Ignagni et al. |
| 2008/0135044 A1 | 6/2008 | Freitag et al. |
| 2008/0139956 A1 | 6/2008 | Diong |
| 2008/0142019 A1 | 6/2008 | Lewis et al. |
| 2008/0156330 A1 | 7/2008 | Smith et al. |
| 2008/0163872 A1 | 7/2008 | Negele et al. |
| 2008/0178880 A1 | 7/2008 | Christopher et al. |
| 2008/0178882 A1 | 7/2008 | Christopher et al. |
| 2008/0185002 A1 | 8/2008 | Berthon-Jones et al. |
| 2008/0216833 A1 | 9/2008 | Pujol et al. |
| 2008/0251078 A1 | 10/2008 | Buckley et al. |
| 2008/0275513 A1 | 11/2008 | Lattner et al. |
| 2008/0281219 A1 | 11/2008 | Glickman et al. |
| 2008/0283061 A1 | 11/2008 | Tiedje |
| 2008/0294060 A1 | 11/2008 | Haro et al. |
| 2008/0295839 A1 | 12/2008 | Habashi |
| 2008/0295840 A1 | 12/2008 | Glaw |
| 2009/0084381 A1 | 4/2009 | DeVries et al. |
| 2009/0107502 A1 | 4/2009 | Younes |
| 2009/0114224 A1 | 5/2009 | Handzsuj et al. |
| 2009/0120439 A1 | 5/2009 | Goebel |
| 2009/0159082 A1 | 6/2009 | Eger |
| 2009/0165795 A1 | 7/2009 | Nadjafizadeh et al. |
| 2009/0171176 A1 | 7/2009 | Andersohn |
| 2009/0173347 A1 | 7/2009 | Berthon-Jones |
| 2009/0188502 A1 | 7/2009 | Tiedje |
| 2009/0205661 A1 | 8/2009 | Stephenson et al. |
| 2009/0205663 A1 | 8/2009 | Vandine et al. |
| 2009/0221926 A1 | 9/2009 | Younes |
| 2009/0229611 A1 | 9/2009 | Martin et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |

(56) References Cited

U.S. PATENT DOCUMENTS

| | | |
|---|---|---|
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0065055 A1 | 3/2010 | Morris et al. |
| 2010/0065057 A1 | 3/2010 | Berthon-Jones |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0137380 A1 | 6/2010 | Maybaum |
| 2010/0137723 A1 | 6/2010 | Patangay et al. |
| 2010/0137729 A1 | 6/2010 | Pierry et al. |
| 2010/0137730 A1 | 6/2010 | Hatlestad |
| 2010/0139660 A1 | 6/2010 | Adahan |
| 2010/0145201 A1 | 6/2010 | Westbrook et al. |
| 2010/0147303 A1 | 6/2010 | Jafari et al. |
| 2010/0152553 A1 | 6/2010 | Ujhazy et al. |
| 2010/0152560 A1 | 6/2010 | Turcott |
| 2010/0174200 A1 | 7/2010 | Wood et al. |
| 2010/0174207 A1 | 7/2010 | Lee et al. |
| 2010/0180898 A1 | 7/2010 | Schneider et al. |
| 2010/0186741 A1 | 7/2010 | Aylesworth et al. |
| 2010/0186742 A1 | 7/2010 | Sherman et al. |
| 2010/0186743 A1 | 7/2010 | Kane et al. |
| 2010/0186744 A1 | 7/2010 | Andrieux |
| 2010/0191076 A1 | 7/2010 | Lewicke et al. |
| 2010/0191137 A1 | 7/2010 | Brada et al. |
| 2010/0192094 A1 | 7/2010 | Jeha et al. |
| 2010/0198086 A1 | 8/2010 | Kuo et al. |
| 2010/0199991 A1 | 8/2010 | Koledin |
| 2010/0210924 A1 | 8/2010 | Parthasarathy et al. |
| 2010/0218764 A1 | 9/2010 | Kwok et al. |
| 2010/0218765 A1 | 9/2010 | Jafari et al. |
| 2010/0218766 A1* | 9/2010 | Milne ............... 128/204.23 |
| 2010/0218767 A1 | 9/2010 | Jafari et al. |
| 2010/0218773 A1 | 9/2010 | Thornton |
| 2010/0222692 A1 | 9/2010 | McCawley et al. |
| 2010/0224190 A1 | 9/2010 | Tilley et al. |
| 2010/0228133 A1 | 9/2010 | Averina et al. |
| 2010/0228134 A1 | 9/2010 | Martikka et al. |
| 2010/0229863 A1 | 9/2010 | Enk |
| 2010/0234750 A1 | 9/2010 | Ariav et al. |
| 2010/0236551 A1 | 9/2010 | Enk |
| 2010/0236554 A1 | 9/2010 | Prete |
| 2010/0236555 A1 | 9/2010 | Jafari et al. |
| 2010/0236556 A1 | 9/2010 | Green et al. |
| 2010/0241009 A1 | 9/2010 | Petkie |
| 2010/0242961 A1 | 9/2010 | Mougel et al. |
| 2010/0242965 A1 | 9/2010 | Berthon-Jones |
| 2010/0249630 A1 | 9/2010 | Droitcour et al. |
| 2010/0249631 A1 | 9/2010 | Aoki et al. |
| 2010/0249632 A1 | 9/2010 | Lee et al. |
| 2010/0249633 A1 | 9/2010 | Droitcour et al. |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252043 A1 | 10/2010 | Freitag |
| 2010/0256463 A1 | 10/2010 | Greenwald et al. |
| 2010/0258116 A1 | 10/2010 | Federspiel et al. |
| 2010/0258124 A1 | 10/2010 | Madaus et al. |
| 2010/0258126 A1 | 10/2010 | Ujhazy et al. |
| 2010/0258127 A1 | 10/2010 | Hk |
| 2010/0262032 A1 | 10/2010 | Freeberg |
| 2010/0282259 A1 | 11/2010 | Figueiredo et al. |
| 2010/0288283 A1 | 11/2010 | Campbell et al. |
| 2010/0300446 A1 | 12/2010 | Nicolazzi et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0216809 A1 | 8/2012 | Milne et al. |

FOREIGN PATENT DOCUMENTS

| | | |
|---|---|---|
| EP | 1005829 A1 | 6/2000 |
| EP | 1005830 A1 | 6/2000 |
| EP | 1491227 | 12/2004 |
| EP | 1277435 B1 | 3/2006 |
| EP | 1515767 | 8/2009 |
| WO | WO9014852 | 12/1990 |
| WO | WO9214505 | 9/1992 |
| WO | WO9308857 | 5/1993 |
| WO | WO9715343 | 5/1997 |
| WO | WO9812965 | 4/1998 |
| WO | WO9951292 | 10/1999 |
| WO | WO9962580 | 12/1999 |

(56) References Cited

FOREIGN PATENT DOCUMENTS

| | | |
|---|---|---|
| WO | WO00/10634 | 3/2000 |
| WO | WO0078380 | 12/2000 |
| WO | WO0174430 | 10/2001 |
| WO | WO0228460 | 4/2002 |
| WO | WO0232488 | 4/2002 |
| WO | WO03008027 | 1/2003 |
| WO | WO2004047621 | 6/2004 |
| WO | WO2005004780 | 1/2005 |
| WO | WO2007102866 | 9/2007 |
| WO | WO2007145948 | 12/2007 |
| WO | WO2008008659 | 1/2008 |
| WO | WO2008021222 | 2/2008 |
| WO | WO2008113752 | 9/2008 |
| WO | WO2009060330 | 5/2009 |

OTHER PUBLICATIONS

7200 Series Ventilator, Options, and Accessories: Operator's Manual, Nellcor Puritan Bennett, Part No. 22300 A, Sep. 1990, pp. 1-196.

7200 Ventilatory System: Addendum/Errata, Nellcor Puritan Bennett, Part No. 4-023576-00, Rev. A, Apr. 1998, pp. 1-32.

800 Operator's and Technical Reference Manual, Series Ventilator System, Nellcor Puritan Bennett, Part No. 4-070088-00, Rev. L, Aug. 2010, pp. 1-476.

840 Operator's and Technical Reference Manual, Ventilator System, Nellcor Puritan Bennett, Part No. 4-075609-00, Rev. G, Oct. 2006, pp. 1-424.

US 7,680,539, 03/2010, Giftakis et al. (withdrawn)

\* cited by examiner

METHODS AND SYSTEMS FOR TRANSITORY VENTILATION SUPPORT

Medical ventilator systems have long been used to provide ventilatory and supplemental oxygen support to patients. These ventilators typically comprise a source of pressurized oxygen which is fluidly connected to the patient through a conduit or tubing. As each patient may require a different ventilation strategy, modern ventilators can be customized for the particular needs of an individual patient. For example, several different ventilator modes have been created to provide better ventilation for patients in various different scenarios.

Transitory Ventilation Support

This disclosure describes systems and methods for providing a transitory ventilation support breath type during ventilation of a patient. The disclosure describes a novel breath type that provides for a beneficial transition between an assist breath type and an effort-based breath type and/or a breath type that is beneficial for weak patients.

In part, this disclosure describes a ventilation system, including: a pressure generating system adapted to generate a flow of breathing gas; a ventilation tubing system including a patient interface for connecting the pressure generating system to a patient; one or more sensors operatively coupled to at least one of the pressure generating system, the patient, and the ventilation tubing system, wherein at least one sensor is capable of generating an output indicative of an inspiration flow; an effort-based ventilation module that calculates at least one target pressure based on at least one measured inspiration flow and causes the pressure generating system to deliver the at least one target pressure to the patient during inhalation; and a transitory ventilation support module that causes the pressure generating system to deliver a control pressure to the patient after a patient initiated trigger is detected for a predetermined amount of time unless the at least one calculated target pressure is greater than a set control pressure during the predetermined amount of time, then the pressure delivered to the patient is determined by the effort-based ventilation module.

Yet another aspect of this disclosure describes a method for ventilating a patient with a ventilator. The method includes:
 a) setting a control pressure;
 b) detecting a patient initiated trigger for a breath;
 c) repeatedly measuring inspiration flows by the patient during delivery of the control pressure starting from the detection of the patient initiated trigger;
 d) calculating target pressures based on each of the measured inspiration flows during the delivery of the control pressure;
 e) repeatedly comparing each calculated target pressure to the control pressure during the delivery of the control pressure;
 f) delivering the control pressure during inhalation for a predetermined amount of time unless at least one of the calculated target pressures is greater than the control pressure; and
 g) delivering a current calculated target pressure during inhalation if the at least one of the calculated target pressures is greater than the control pressure.

In yet another aspect, the disclosure describes a computer-readable medium having computer-executable instructions for performing a method for ventilating a patient with a ventilator. The method includes:

a) repeatedly detecting a patient initiated trigger for a breath;
 b) repeatedly measuring inspiration flows by the patient during delivery of a control pressure starting from the detection of the patient initiated trigger;
 c) repeatedly calculating target pressures based on each of the measured inspiration flows during the delivery of the control pressure;
 d) repeatedly comparing each calculated target pressure to the control pressure during the delivery of the control pressure;
 e) repeatedly delivering the control pressure during inhalation for a predetermined amount of time unless at least one of the calculated target pressures is greater than the control pressure; and
 f) repeatedly delivering a current calculated target pressure during inhalation if the at least one of the calculated target pressures is greater than the control pressure.

In an additional aspect, the disclosure describes a ventilation system that includes: means for setting a control pressure; means for detecting a patient initiated trigger for a breath; means for repeatedly measuring inspiration flows by the patient during delivery of the control pressure starting from the detection of the patient initiated trigger; means for calculating target pressures based on each of the measured inspiration flows during the delivery of the control pressure; means for repeatedly comparing each calculated target pressure to the control pressure during the delivery of the control pressure; means for delivering the control pressure during inhalation for a predetermined amount of time unless at least one of the calculated target pressures is greater than the control pressure; and means for delivering a current calculated target pressure during inhalation if the at least one of the calculated target pressures is greater than the control pressure.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of embodiments of systems and methods described below and are not meant to limit the scope of the invention in any manner, which scope shall be based on the claims appended hereto.

DETAILED DESCRIPTION

Although the techniques introduced above and discussed in detail below may be implemented for a variety of medical devices, the present disclosure will discuss the implementation of these techniques in the context of a medical ventilator for use in providing ventilation support to a human patient. The reader will understand that the technology described in the context of a medical ventilator for human patients could be adapted for use with other systems such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

While operating a ventilator, it is desirable to control the percentage of oxygen in the gas supplied by the ventilator to the patient. Further, as each patient may require a different ventilation strategy, modern ventilators can be customized for the particular needs of an individual patient. For example, several different ventilator breath types have been created to provide better ventilation for patients in various different scenarios.

Effort-based breath types, such as proportional assist (PA) ventilation, determine a dynamic profile of ventilatory support derived from continuous estimation of patient effort and respiratory characteristics. This desired dynamic profile is computed in real- or quasi-real-time and used by the ventilator as a set of points for control of applicable parameters.

Initiation and execution of an effort-based breath, such as PA, has two operation prerequisites: (1) detection of an inspiratory trigger, and (2) detection and measurement of an appreciable amount of patient respiratory effort to constitute a sufficient reference above ventilator's control signal error deadband. Advanced, sophisticated triggering technologies detect initiation of inspiratory efforts more efficiently. Any suitable type of triggering detection for determining a patient trigger may be utilized by the ventilation system, such as nasal detection, diaphragm detection, and/or brain signal detection. In ventilation design, patient effort may be represented by the estimated inspiratory muscle pressure and is calculated based on measured patient inspiration flow. Patient effort is utilized to calculate a target pressure for the inspiration. However, while earlier trigger detection reduces trigger delays, the corresponding inspiration flow at this earlier moment of triggering may be initially too weak to measure its magnitude and/or the algebraic magnitude of estimated lung flow may be still negative resulting in the premature ending of a patient desired breath. In the absence of a measurable positive inspiration flow at the detection of an inspiratory trigger, the ventilator needs a reference support trajectory to deliver until a consistent measurable effort is sensed to transition into a conventional effort-based breath.

Accordingly, the current disclosure describes a transitory ventilation support setting to enable execution and delivery of effort-based breaths when initial inspiration flow and thereby patient effort does not reach an operational minimum threshold required for pneumatic control.

Figure 1:
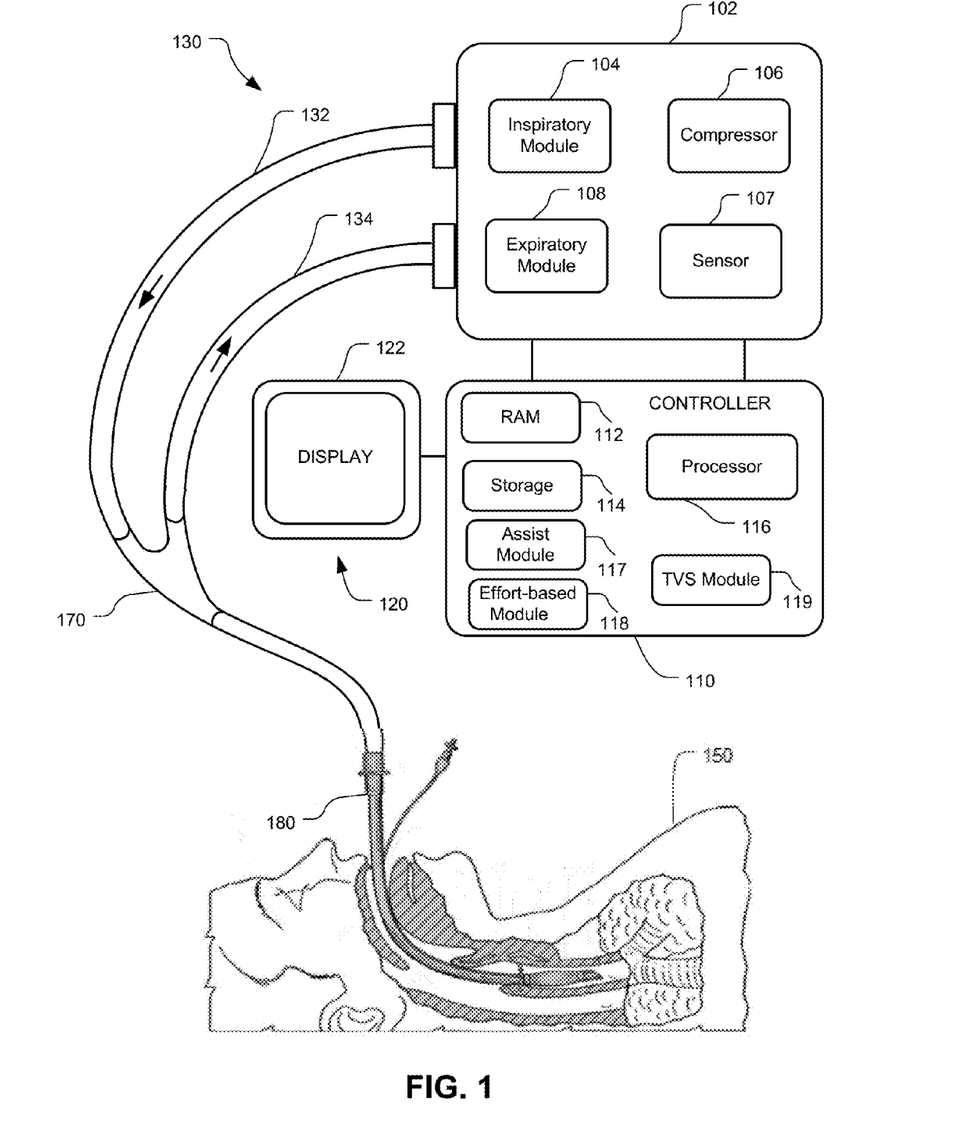
FIG. 1 illustrates an embodiment of a ventilator for delivering a transitory ventilation support breath type.

FIG. 1 is a diagram illustrating an embodiment of an exemplary ventilator 100 connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180.

Ventilation tubing system 130 (or patient circuit 130) may be a two-limb (shown) or a one-limb circuit for carrying gases to and from the patient ISO. In a two-limb embodiment, a fitting, typically referred to as a "wye-fitting" 170, may be provided to couple a patient interface 180 (as shown, an endotracheal tube) to an inspiratory limb 132 and an expiratory limb 134 of the ventilation tubing system 130.

Pneumatic system 102 may be configured in a variety of ways. In the present example, pneumatic system 102 includes an expiratory module 108 coupled with the expiratory limb 134 and an inspiratory module 104 coupled with the inspiratory limb 132. Compressor 106 or other source(s) of pressurized gases (e.g., air, oxygen, and/or helium) is coupled with inspiratory module 104 and the expiratory module 108 to provide a gas source for ventilatory support via inspiratory limb 132.

The inspiratory module 104 is configured to deliver gases to the patient 150 according to prescribed ventilatory settings. In some embodiments, inspiratory module 104 is configured to provide ventilation according to various breath types, e.g., via volume-control, pressure-control, or via any other suitable breath types.

The expiratory module 108 is configured to release gases from the patient's lungs according to prescribed ventilatory settings. Specifically, expiratory module 108 is associated with and/or controls an expiratory valve for releasing gases from the patient 150.

The ventilator 100 may also include one or more sensors 107 communicatively coupled to ventilator 100. The sensors 107 may be located in the pneumatic system 102, ventilation tubing system 130, and/or on the patient 150. The embodiment of FIG. 1, illustrates a sensor 107 in pneumatic system 102.

Sensors 107 may communicate with various components of ventilator 100, e.g., pneumatic system 102, other sensors 107, processor 116, transitory ventilation support (TVS) module 119, and any other suitable components and/or modules. In one embodiment, sensors 107 generate output and send this output to pneumatic system 102, other sensors 107, processor 116, TVS module 119, and any other suitable components and/or modules. Sensors 107 may employ any suitable sensory or derivative technique for monitoring one or more parameters associated with the ventilation of a patient 150. Sensors 107 may detect changes in ventilatory parameters indicative of patient triggering, for example. Sensors 107 may be placed in any suitable location, e.g., within the ventilatory circuitry or other devices communicatively coupled to the ventilator 100. Further, sensors 107 may be placed in any suitable internal location, such as, within the ventilatory circuitry or within components or modules of ventilator 100. For example, sensors 107 may be coupled to the inspiratory and/or expiratory modules for detecting changes in, for example, circuit pressure and/or flow. In other examples, sensors 107 may be affixed to the ventilatory tubing or may be embedded in the tubing itself. According to some embodiments, sensors 107 may be provided at or near the lungs (or diaphragm) for detecting a pressure in the lungs. Additionally or alternatively, sensors 107 may be affixed or embedded in or near wye-fitting 170 and/or patient interface 180. Indeed, any sensory device useful for monitoring changes in measurable parameters during ventilatory treatment may be employed in accordance with embodiments described herein.

As should be appreciated, with reference to the Equation of Motion, ventilatory parameters are highly interrelated and, according to embodiments, may be either directly or indirectly monitored. That is, parameters may be directly monitored by one or more sensors 107, as described above, or may be indirectly monitored by derivation according to the Equation of Motion.

The pneumatic system 102 may include a variety of other components, including mixing modules, valves, tubing, accumulators, filters, etc. Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.).

In one embodiment the operator interface 120 of the ventilator 100 includes a display 122 communicatively coupled to ventilator 100. Display 122 provides various input screens, for receiving clinician input, and various display screens, for presenting useful information to the clinician. In one embodiment, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display 122. Display 122 may also provide useful information in the form of various ventilatory data regarding the physical condition of a patient. The useful information may be derived by the ventilator 100, based on data collected by a processor 116, and the useful information may be displayed to the clinician in the form of graphs, wave representations, pie graphs, or other suitable forms of graphic display. For example, patient data may be displayed on the GUI and/or display 122. Additionally or alternatively, patient data may be communicated to a remote monitoring system coupled via any suitable means to the ventilator 100.

Controller 110 may include memory 112, one or more processors 116, storage 114, and/or other components of the type commonly found in command and control computing devices. Controller 110 may further include an assist ventilation module 117, an effort-based ventilation module 118, and a transitory ventilation support (TVS) module 119 configured to deliver gases to the patient 150 according to prescribed breath types as illustrated in FIG. 1. In alternative embodiments, the assist ventilation module 117, the effort-based ventilation module 118, and the TVS module 119 configured to deliver gases to the patient 150 according to prescribed breath types may be located in other components of the ventilator 100, such as the pressure generating system 102 (also known as the pneumatic system 102).

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

In one embodiment, the inspiratory module 104 receives a breath type from the assist ventilation module 117, the effort-based ventilation module 118, and the TVS module 119. The assist ventilation module 117 provides assist breath types, such as volume-based ventilation breath types and pressure-based ventilation breath types. The effort-based ventilation module 118 provides ventilation based on patient effort, such as PA. The TVS module 119 provides a transitory breath type that helps a patient transition from an assist-based breath type to an effort-based breath type. The purpose of the TVS breath type is to form a bridge between the point at which a breath is triggered and the point at which there is sufficient effort detected to begin delivery of an effort-based breath. We are using the term "breath type" in relation to TVS instead of such terms as "profile" or "algorithm" to highlight the possibility that, in the event of a very weak breathing patient, in fact no transition to an effort-based breath type may occur—thus causing an entire breath to be delivered according to the TVS breath type. However, for patients with sufficient effort, it is anticipated that the TVS breath type will be delivered to a patient for only a short period of time, if at all, at the beginning of an effort-based breath.

In some embodiments, the assist ventilation module 117 provides a volume-based breath type. Volume ventilation refers to various forms of volume-targeted ventilation that regulate volume delivery to the patient. Different types of volume ventilation are available depending on the specific implementation of volume regulation. For example, for volume-cycled ventilation, an end of inspiration is determined based on monitoring the volume delivered to the patient. Volume ventilation may include volume-control (VC), volume-targeted-pressure-control (VC+), or volume-support (VS) breath types.

According to alternative embodiments, the assist ventilation module 117 provides the inspiratory module 104 with a pressure-based breath type for pressure ventilation. Pressure-targeted types of ventilation may be provided by regulating the pressure delivered to the patient in various ways. For example, during pressure-cycled ventilation, an end of inspiration is determined based on monitoring the pressure delivered to the patient. Pressure ventilation may include pressure-support (PS) and pressure-control (PC) breath types, for example.

The effort-based ventilation module 118 provides an effort-based breath type to the inspiratory module 104. Initiation and execution of an effort-based breath, has two operation prerequisites: (1) detection of an inspiratory trigger, and (2) detection and measurement of an appreciable amount of patient respiratory effort to constitute a sufficient reference above ventilator's control signal error deadband. Patient effort is calculated based on a measured patient inspiration flow. Patient effort is utilized to calculate a target pressure for the inspiration. In addition, the sensitivity of the ventilator to changes in patient effort may be adjusted such that the ventilator may properly detect the patient effort. For example, the lower the pressure or flow change threshold setting, the more sensitive the ventilator may be to patient effort. However, each ventilator will have a minimum measurable inspiration flow and thereby patient effort that the ventilator can detect. An inspiration flow or patient effort below this minimum will not be detected by the ventilator.

Any suitable type of triggering detection for determining a patient trigger may be utilized by the ventilation system, such as nasal detection, diaphragm detection, and/or brain signal detection. Further, the ventilator 100 may detect patient triggering via a pressure-monitoring method, a flow-monitoring method, direct or indirect measurement of neuromuscular signals, or any other suitable method. Sensors suitable for this detection may include any suitable sensing device as known by a person of skill in the art for a ventilator. According to an embodiment, a pressure-triggering method may involve the ventilator monitoring the circuit pressure, and detecting a slight drop in circuit pressure. The slight drop in circuit pressure may indicate that the patient's respiratory muscles are creating a slight negative pressure, $P_m$, that in turn generates a pressure gradient between the patient's lungs and the airway opening in an effort to inspire. The ventilator may interpret the slight drop in circuit pressure as a patient trigger and may consequently initiate inspiration by delivering respiratory gases.

Alternatively, the ventilator may detect a flow-triggered event. Specifically, the ventilator may monitor the circuit flow, as described above. If the ventilator detects a slight drop in the base flow through the exhalation module during exhalation, this may indicate, again, that the patient is attempting to inspire. In this case, the ventilator is detecting a drop in bias flow (or baseline flow) attributable to a slight redirection of gases into the patient's lungs (in response to a slightly negative pressure gradient as discussed above). Bias flow refers to a constant flow existing in the circuit during exhalation that enables the ventilator to detect expiratory flow changes and patient triggering.

In some embodiments, the effort-based breath type is a PA or a PA+ breath type. The proportional assist (PA) breath type provides pressure in proportion to the instantaneous patient effort during spontaneous ventilation and is based on the equation of motion. The PA+ breath type is the same as the PA breath type except that the PA+ breath type compensates for tubing system leakage. The PA+ breath type described herein may be the systems and methods of ventilation described in U.S. application Ser. No. 12/408,408, filed on Mar. 20, 2009 and entitled "Leak-Compensated Proportional Assist Ventilation", which is incorporated herein by reference in its entirety.

In mechanical ventilation, a proportional assist (PA) breath type refers to a type of ventilation in which the ventilator acts as an inspiratory amplifier that provides pressure support based on the patient's effort. The degree of amplification (the "support setting") is set by an operator, for example as a percentage based on the patient's effort. In one implementation of a PA breath type, the ventilator may continuously monitor the patient's instantaneous inspiratory flow and instantaneous net lung volume, which are indicators of the patient's inspiratory effort. These signals, together with ongoing estimates of the patient's lung compliance and lung resistance, allow the ventilator to compute a patient effort and derive therefrom a target pressure to provide the support that assists the patient's inspiratory muscles to the degree selected by the operator as the support setting.

Various methods are known for calculation of patient effort and any suitable method may be used. For example, methods exist that calculate patient effort from sensors attached to the body to detect neural or muscular activity as well as methods that determine a patient effort based on respiratory flow, respiratory pressure or a combination of both flow and pressure. The transitory ventilation techniques for providing PA breaths described herein may be adapted to use any such known method.

PA relies on certain physiological principles. The act of inspiration requires the patient's inspiratory muscles to develop a pressure gradient between the mouth and the alveoli sufficient to draw in breathing gas and inflate the lungs. The ventilator providing PA may use specific information, including resistance of the artificial airway, resistance of the patient's airways, lung compliance, instantaneous inspiratory flow and net lung volume, and the support setting to compute the target pressure to be applied at the wye. In one implementation, every computational cycle (e.g., 5 milliseconds, 10 milliseconds, etc.), the ventilator estimates target pressure, based on instantaneous inspiratory flow and net lung volume.

PA begins inspiratory assist when a trigger is detected and when inspiration flow (generated by the patient's inspiratory muscles) is detected. If the patient ceases inspiration, the assist also ceases. This functionality is often a problem for weak patients. Weak patients may begin inhaling while still exhaling. This creates a negative inhalation flow that is interpreted by the ventilator as the ceasing of inspiration or as a negative target pressure, which will prematurely end a patient desired breath provided by the PA breath type or otherwise prevent the ventilator from delivering pressure because the patient effort signal is too low. Once a measurable, positive inspiration flow is detected by the ventilator, the ventilator applies the calculated target pressure to deliver a proportion (determined by the support setting) of the total demand as determined by the patient's inspiratory effort.

The TVS module 119 provides a TVS breath type for weak patients to the inspiratory module 104 that initially provides an assist based breath type which then transitions to an effort-based breath type during inhalation. As discussed above, initiation and execution of an effort-based breath, such as PA, has two operation prerequisites: (1) detection of an inspiratory trigger, and (2) detection and measurement of an appreciable amount of patient respiratory effort to constitute a sufficient reference above the ventilator's control error deadband. Advanced, sophisticated triggering technologies detect initiation of inspiratory efforts more efficiently and in some cases independently of the measurement of patient respiratory effort and/or inspired flow. However, while earlier detection of an inspiratory effort reduces trigger delays, the measurement of patient respiratory effort (e.g., inspiration flow) at this earlier time of triggering may initially be so weak that the ventilator may not be able to measure its magnitude. Further, due to early detection, the inspiration flow at the time of triggering may be negative if the patient triggered inhalation while still exhaling. In the case of using inspiratory flow as the measurement of patient effort, a positive, measurable inspiration flow is necessary for the effort-based breath type to deliver a breath. It should be noted that the actual threshold used will be dependent on the measurement of patient effort used for the effort-based breath. Accordingly, during these scenarios the patient does not receive a breath as desired from the ventilator.

Accordingly, the TVS module 119 provides a support trajectory before initiating the conventional effort-based breath. The TVS breath type provided by the TVS module 119 has a set control pressure, which exceeds the ventilator system's minimum error sensitivity threshold. The TVS breath type provides inspiration at the set control pressure until a predetermined inspiratory time expires or until a target pressure calculated by the effort-based breath type exceeds the set control pressure for at least a minimum set time window (for example 25 or 50 ms) prior to the expiration of the predetermined inspiration time. As discussed above, the target pressure is calculated based on the patient effort, which in this embodiment is based on inspiration flow by the effort-based breath type.

In some embodiments, the control pressure is set by the operator, selected by the operator, or set by the ventilator. In some embodiments, the predetermined duration of time for the TVS breath is set by the operator, selected by the operator, or set by the ventilator. As used herein any threshold, condition, setting, parameter, and/or frequency that are "predetermined" may be input or selected by the operator and/or may be set or selected by the ventilator. In further embodiments, the predetermined duration of time for the TVS breath is set and/or selected by the ventilator or operator based on at least one patient parameter, such as IBW, height, weight, disease condition, and etc. In other embodiments, the predetermined amount of time is 200 milliseconds (ms) or 250 ms. The TVS breath may be volume controlled (VC), pressure controlled (PC), volume-targeted pressure controlled (VC+), or any other suitable type.

During this breath type, the alarm settings are identical to the alarm settings for a PC or VC breath. In some embodiments, the alarm settings are based on the most recently utilized breath type prior to the TVS breath type. Further, the remaining ventilator settings and/or parameters either remain as set by the operator or are the fixed default values provided by the ventilator.

As described above, the TVS breath type is particularly useful for weak patients, who may begin inhalation before they finish exhaling or who are too weak to provide a patient effort at a measureable magnitude, but sufficient enough for trigger detection. For example, weak patients may include adult patients with COPD or neonates with chest wall distortion.

In some embodiments, the TVS module 119 activates and/or deactivates a TVS breath type upon operator selection. The activation and/or deactivation is performed by a switch within the ventilator 100. The switch may be any suitable means, software, and/or hardware for activating and/or deactivating the TVS breath type. In further embodiments, the TVS module 119 activates and/or deactivates a TVS breath type automatically to transition between assist breath types and effort-based breath types. In some embodiments, while utilizing the TVS breath type, the ventilator may never transition to an effort-based breath type and may stay in the TVS breath type or transition back to the assist breath type after a predetermined amount time elapses or a predetermined number of breaths occur. For example, in an embodiment if the target pressure does not rise above the control pressure within a breath or in some predetermined number of breaths, the ventilator may automatically revert to delivery of an assist breath after delivery of the TVS breath.

The TVS module 119 transitions between an assist breath type to a TVS breath type by any suitable means, such as at or before a patient initiated trigger. In some embodiments, the TVS module 119 initiates the transition between an assist breath type and the TVS breath type upon detection of a patient initiated breath or after a pattern of patient initiated breaths are detected.

Figure 2:
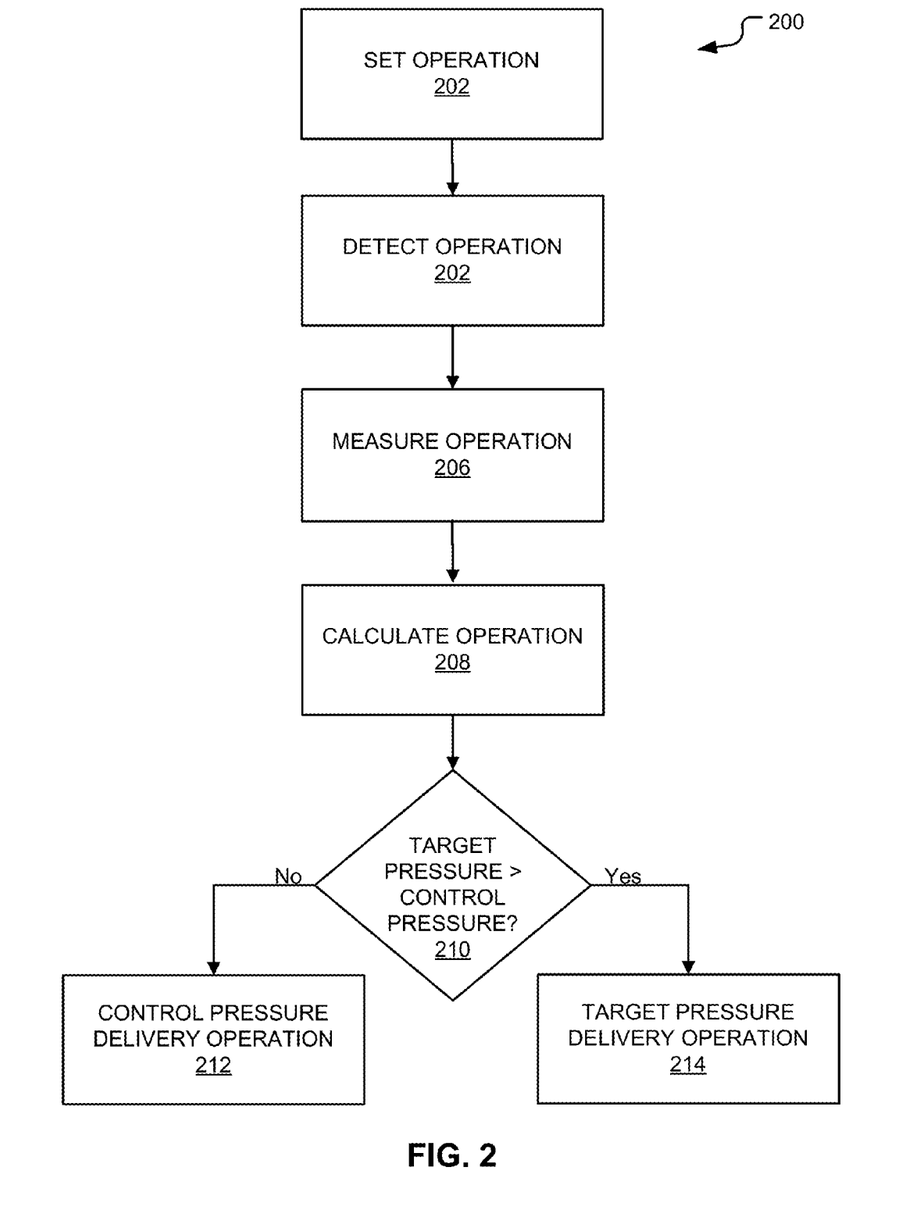
FIG. 2 illustrates an embodiment of a method for ventilating a patient that utilizes a transitory ventilation support breath type.

FIG. 2 illustrates an embodiment of a method 200 for ventilating a patient with a ventilator that utilizes a transitory ventilation support breath type. As illustrated, method 200 includes a setting operation 202. During the setting operation 202, the ventilator determines or receives a set control pressure. The set control pressure exceeds the ventilator's minimum error sensitivity threshold. In some embodiments, the control pressure is set by the operator, selected by the operator, or set by the ventilator. In some embodiments, the control pressure is set by receiving input from an operator via a user interface.

Further, method 200 includes a detecting operation 204. During the detecting operation 204, the ventilator detects a patient initiated trigger for a breath. The detect operation 204 may be performed by the ventilator during the exhalation phase of any breath type. The ventilator may detect a patient trigger by any suitable means for detecting a patient trigger, such as nasal detection, diaphragm detection, and/or brain signal detection. Further, the ventilator during detecting operation 204 may detect patient triggering via a pressure-monitoring method, a flow-monitoring method, a combination method in which triggering is based on both pressure and flow, direct or indirect measurement of nerve impulses, or any other suitable method. The triggering detection is based on sensor readings. Sensors may include any suitable sensing device as known by a person of skill in the art for a ventilator.

Next, method 200 includes a measure operation 206. During the measure operation 206, the ventilator measures inspiration flows during delivery of the control pressure starting from the detection of the patient initiated trigger. Inspiration flow is generated by the patient's inspiratory muscles. In some embodiments, the ventilator during the measure operation 206 measures the inspiration flow every computational cycle (e.g., 2 milliseconds, 5 milliseconds, 10 milliseconds, etc.) during the delivery of the control pressure. Advanced, sophisticated triggering technologies detect initiation of inspiratory efforts more efficiently. However, while earlier detection of an inspiratory effort reduces trigger delays, the inspiratory flow at the time of triggering may initially be so weak that the ventilator may not be able to measure its magnitude. Further, the inspiratory flow at the time of triggering may be negative if the patient triggers inhalation while still exhaling. Further, if the patient ceases inspiration, the inspiration flow is zero.

Next, method 200 includes a calculating operation 208. During the calculating operation 208, the ventilator calculates target pressures based on each of the measured inspiration flows during the delivery of the control pressure. The patient's inspiratory or inspiration flow and net lung volume are indicators of the patient's inspiratory effort. These signals, together with ongoing estimates of the patient's lung compliance and lung resistance, allow the ventilator to compute a target pressure at a point in the ventilation circuit that assists the patient's inspiratory muscles to the degree selected by the operator as the support setting. In some embodiments, the target pressure calculation is based on an effort based breath type. In further embodiments, the target pressure calculation is based on a PA or PA+ breath type.

Next, method 200 includes a determination operation 210. During the determination operation 210, the ventilator compares each calculated target pressure to the control pressure during the delivery of the control pressure. If the ventilator during the determination operation 210 determines that at least one of the calculated target pressures is greater than the set control pressure, then the ventilator performs target pressure delivery operation 214. If the ventilator during the determination operation 210 determines that none of the calculated target pressures are equal to or less than the set control pressure, then the ventilator performs control pressure delivery operation 212 until the predetermined amount of time expires or, for example, until the ventilator detects that the at least one of the calculated target pressures is greater than the set control pressure within the predetermined amount of time. In an alternative embodiment, different threshold criteria may be used such as requiring that all of the calculated target pressures must be greater than the set control pressure for the effort-based breath type to be delivered.

The at least one of the calculated target pressures may be a single target pressure or may be a predetermined pattern of target pressures. Accordingly, the ventilator during the determination operation 210 will not determine that the at least one of the calculated target pressures is greater than the set control pressure until the pattern of target pressures is met. For example, the predetermined pattern of calculated target pressures may be two or more consecutive calculated target pressures measuring more than a predetermined level (e.g., 0.30 cm $H_2O$) above the control pressure. In another example, the predetermined pattern of calculated target pressures may be any two calculated target pressures measuring more than 1 cm $H_2O$ above the control pressure within a predetermined time period, such as 30 ms.

The ventilator continues to perform the determination operation 214 until the predetermined amount of time expires or until the ventilator detects that the at least one of the target pressures is greater than the set control pressure. Further, the ventilator continues to perform the measuring operation 206 and the calculating operation 208 until the predetermined amount of time expires or until the ventilator detects that at least one of the target pressures is greater than the set control pressure during determination operation 214.

Method 200 includes a control pressure delivery operation 212. During the control pressure delivery operation 212, the ventilator delivers the control pressure during inhalation for the predetermined amount of time or until the ventilator detects that the at least one of the target pressures is greater than the set control pressure within the predetermined amount of time. If the predetermined amount of time expires, then ventilator cycles to exhalation, which restarts method 200. During the delivery of the control pressure the ventilator executes alarms according to an assist breath type, such as VC, PC, etc. In some embodiment, the ventilator may execute alarms based on the most recently utilized assist breath type.

In some embodiments, the predetermined amount of time is set by the operator, selected by the operator, or set by the ventilator. In further embodiments, the predetermined amount of time is set and/or selected by the ventilator or operator based on at least one patient parameter, such as IBW, height, weight, disease condition, and etc. In other embodiments, the predetermined amount of time is 200 ms or 250 ms.

In some embodiments, method 200 further includes an assist determination operation. The ventilator during the assist determination operation detects if the target pressures are never greater than the control pressure for a predetermined period of time or for a predetermined number of breaths. If the ventilator detects during the assist determination operation, that the target pressures are never greater than the control pressure for a predetermined period of time or for a predetermined number of breaths, then the ventilator may be switched to a mode that delivers only the assist breath type, such as PC or VC. In some embodiments, the ventilator switches to the most recently utilized assist breath type. For example, if the ventilator detects during the assist determination operation, that at least one of the target pressures are greater than the control pressure for the predetermined period of time or for the predetermined number of breaths, then the ventilator continues to provide a TVS breath type.

Method 200 includes a target pressure delivery operation 214. During the target pressure delivery operation 214, the ventilator delivers a current calculated target pressure during inspiration. The current target pressure is the most recently calculated target pressure. In some embodiments, the calculation and delivery of the target pressure is based on an effort-based breath type, such PA, PA+, etc. In some embodiments, the ventilator executes alarms or advisory notices based on an effort-based breath type (e.g., PA, PA+, etc.) during the delivery of the current target pressure. In some embodiments, the ventilator executes alarms based on a PA breath type during the delivery of the current target pressure. The breath will cycle to exhalation after the delivery of the target pressure based on the procedures for any effort-based breath, which restarts method 200.

In one embodiment, a portion of the steps (e.g., 204 through 214) of method 200 are performed by a computer-readable medium having computer-executable instructions. In another embodiment, the ventilator system includes means for performing the steps of method 200. The means for performing the steps of method 200 are disclosed above, such as in ventilator 100.

In another embodiment, the ventilator system includes means for setting a control pressure; means for detecting a patient initiated trigger for a breath; means for repeatedly measuring inspiration flows by the patient during delivery of the control pressure starting from the detection of the patient initiated trigger; means for calculating target pressures based on each of the measured inspiration flows during the delivery of the control pressure; means for repeatedly comparing each calculated target pressure to the control pressure during the delivery of the control pressure; means for delivering the control pressure during inhalation for a predetermined amount of time unless at least one of the calculated target pressures is greater than the control pressure; and means for delivering a current calculated target pressure during inhalation if the at least one of the calculated target pressures is greater than the control pressure.

EXAMPLE 1

Figure 3:
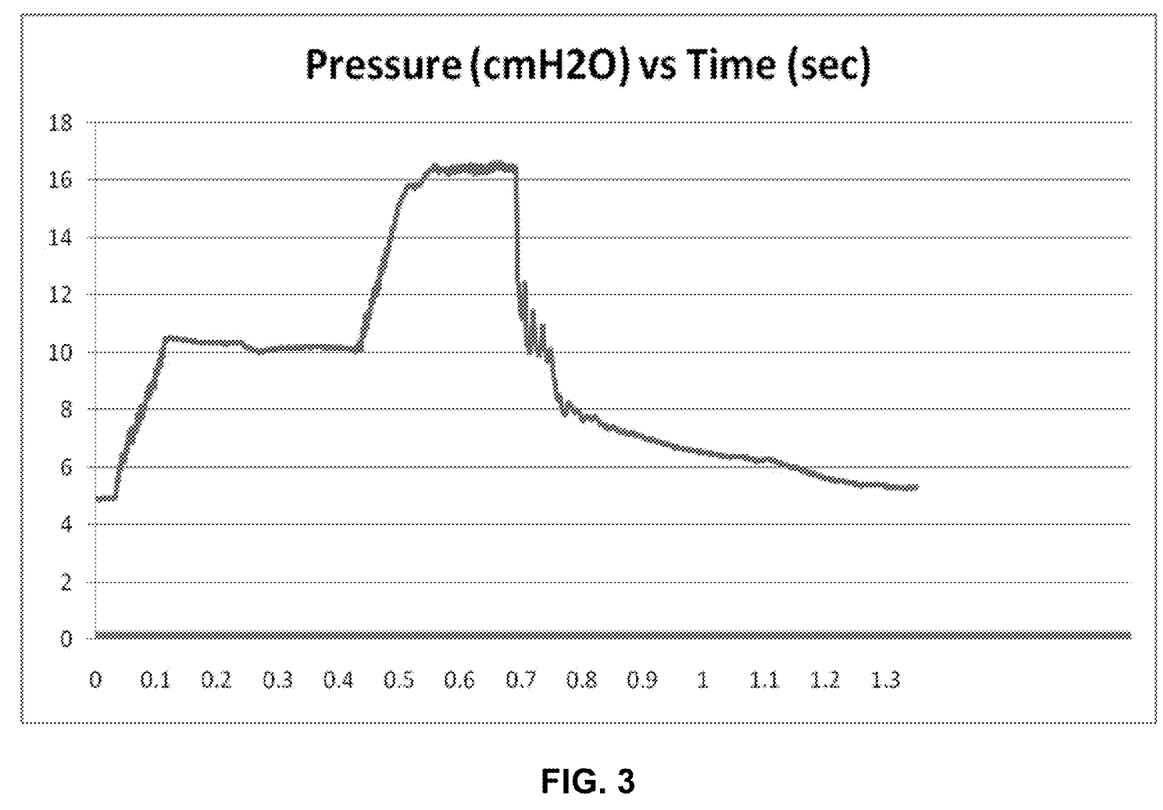
FIG. 3 illustrates an embodiment of a pressure waveform showing a change from inspiration to exhalation.

FIG. 3 illustrates an embodiment of a pressure waveform showing a change from inspiration to expiration. During inspiration, the pressure waveform illustrates a transition from a TVS breath type to an effort-based breath type. The effort-based breath type begins around 0.4 seconds.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software or firmware components described herein as would be understood by those skilled in the art now and hereafter.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

What is claimed is:

1. A ventilator system comprising:
   a pressure generating system adapted to generate a flow of breathing gas;
   a ventilation tubing system including a patient interface for connecting the pressure generating system to a patient;
   one or more sensors operatively coupled to at least one of the pressure generating system, the patient, and the ventilation tubing system, wherein at least one sensor is capable of generating an output indicative of an inspiration flow;
   an effort-based ventilation module that calculates at least one target pressure based on at least one measured inspiration flow and causes the pressure generating system to deliver the at least one target pressure to the patient during inhalation; and
   a transitory ventilation support module provides a support trajectory for an effort-based delivered breath, the transitory ventilation support module causes the pressure generating system to deliver a control pressure to the patient after a patient initiated trigger is detected for a predetermined amount of time unless the at least one calculated target pressure is greater than a set control pressure during the predetermined amount of time, then a pressure delivered to the patient is determined by the effort-based ventilation module.

2. The method of claim 1, further comprising a switch for activating and deactivating the transitory ventilation support module.

3. The method of claim 1, wherein the ventilator system automatically utilizes the transitory ventilation support module unless deactivated by an operator.

4. The method of claim 1, wherein the at least one sensor generates the output indicative of the inspiration flow every 5 ms during the predetermined amount of time.

5. The method of claim 1, wherein the predetermined amount of time is based on a patient parameter.

6. A ventilator system, comprising:
   means for setting a control pressure;
   means for detecting a patient initiated trigger for a breath;
   means for repeatedly measuring inspiration flows by a patient during delivery of the control pressure starting from a detection of the patient initiated trigger;
   means for calculating target pressures based on each measured inspiration flows during the delivery of the control pressure;
   means for comparing each calculated target pressure to the control pressure during the delivery of the control pressure;
   means for delivering the control pressure during inhalation for a predetermined amount of time unless at least one of the calculated target pressures is greater than the control pressure and
   for delivering a current calculated target pressure during inhalation if the at least one of the calculated target pressures is greater than the control pressure.

* * * * *